United States Patent [19]

Gould

[11] 3,932,540
[45] Jan. 13, 1976

[54] PROCESS FOR THE PRODUCTION OF 2,3-DIBROMO-1-PROPANOL
[75] Inventor: Henry Gould, Englishtown, N.J.
[73] Assignee: Tenneco Chemicals, Inc., Saddle Brook, N.J.
[22] Filed: May 13, 1974
[21] Appl. No.: 469,353

[52] U.S. Cl................................. 260/633; 260/652
[51] Int. Cl.$^2$........................................ C07C 31/34
[58] Field of Search..................................... 260/633

[56] References Cited
UNITED STATES PATENTS

| | | | |
|---|---|---|---|
| 3,268,597 | 8/1966 | Clemons et al. | 260/633 |
| 3,283,013 | 11/1966 | Rimmer | 260/633 |
| 3,378,593 | 4/1968 | Jenkner et al. | 260/633 |

OTHER PUBLICATIONS

Hickinbottom, Reactions of Organic Compounds, Longmans, Green & Co., (1950), p. 3.

*Primary Examiner*—Howard T. Mars
*Attorney, Agent, or Firm*—Evelyn Berlow

[57] ABSTRACT

2,3-Dibromo-1-propanol of at least 99.5% purity is prepared in high yeilds by continuously adding bromine and allyl alcohol to a reactor that contains a reaction medium that is immiscible with 2,3-dibromo-1-propanol and inert to bromine and continuously removing 2,3-dibromo-1-propanol from the reactor.

8 Claims, No Drawings

PROCESS FOR THE PRODUCTION OF 2,3-DIBROMO-1-PROPANOL

This invention relates to a process for the production of 2,3-dibromo-1-propanol.

Tris-(2,3-dibromopropyl)phosphate, which is a valuable flame-proofing agent for textiles and for various resins, is generally prepared by the reaction of 2,3-dibromo-1-propanol with phosphorus oxychloride. To avoid the formation of undesirable by-products of this reaction, it is necessary that the 2,3-dibromo-1-propanol that is esterified contain very small amounts of 1,2,3-tribromopropane and other volatile impurities.

2,3-Dibromo-1-propanol is readily prepared by the bromination of allyl alcohol. This bromination, however, is usually accompanied by side reactions which lead to the formation of 1,2,3-tribromopropane, allyl bromide, 1,2-dibromopropane, and 1,3-dibromo-2-propanol.

Since it is difficult and costly to separate the reaction by-products from 2,3-dibromo-1-propanol, attempts have been made to develop processes that yield a maximum amount of 2,3-dibromo-1-propanol and a minimum amount of 1,2,3-tribromopropane and other reaction by-products. The batch processes described in the prior art involve the reaction of bromine with allyl alcohol in the absence of a solvent or in the presence of a small amount of a solvent. These processes are not satisfactory because they give relatively low yields of products that contain more than 10 percent of 1,2,3-tribromopropane. In U.S. Pat. No. 3,268,597, Clemons et al. disclosed a continuous process for the bromination of allyl alcohol in the presence of 2,3-dibromo-1-propanol. The product of this process, which was obtained in yields of about 78 percent to 86 percent, contained from 2 percent to 5 percent of 1,2,3-tribromopropane. Another continuous process for the production of 2,3-dibromo-1-propanol, which was described by Jenkner et al. in U.S. Pat. No. 3,378,593, calls for the addition of bromine to a mixture of allyl alcohol and 2,3-dibromo-1-propanol, and it yields a product that contains about 5 percent of low-boiling impurities.

In accordance with this invention, a process has been developed for the production of 2,3-dibromo-1-propanol of excellent quality in high yields. This process, which is preferably carried out continuously, is simple and economical from the viewpoint of equipment, material, and labor costs, and it can be carried out in a single vessel with a high volume output. This process overcomes the difficulties of the prior art processes in that it suppresses side reactions and the formation of undesirable by-products.

In the practice of the process of this invention in a continuous manner, bromine and allyl alcohol in the amounts of about 0.95 mole to 1.05 moles of bromine per mole of allyl alcohol are added simultaneously and continuously to a vessel that contains a reaction medium that is immiscible with 2,3-dibromo-1-propanol and inert to bromine, and the 2,3-dibromo-1-propanol that forms is removed continuously from the reaction vessel.

During the bromination of allyl alcohol, the reaction mixture is agitated vigorously and maintained at a temperature in the range of −10°C. to 60°C., and preferably in the range of 10°C. to 40°C.

The bromine and allyl alcohol that are added to the reaction medium react rapidly to form 2,3-dibromo-1-propanol. Shortly after the addition of bromine and allyl alcohol is begun, the reaction mixture separates into two phases. The lower phase comprises 2,3-dibromo-1-propanol, and the upper phase comprises the reaction medium. As the addition of bromine and allyl alcohol proceeds, the additional quantities of the lower 2,3-dibromo-1-propanol layer that are formed are removed from the reaction vessel. Because the product layer is removed continuously at approximately the rate at which it is formed, a small reaction vessel can be used to produce large quantities of 2,3-dibromo-1-propanol.

The crude product that is removed from the reaction vessel is heated under subatmospheric pressure to separate from it the small amounts of the reaction medium and of low-boiling impurities that it contains. After removal of low-boilers the desired product is collected as a distillate of at least 99.5 percent and in most cases 99.7 percent or more of 2,3-dibromo-1-propanol. It can be used without further purification in the production of tris(2,3-dibromopropyl)phosphate, The reaction medium in which the bromination of allyl alcohol is effected is a liquid that is immiscible with 2,3-dibromo-1-propanol and inert to bromine. The medium may be, for example, a saturated aliphatic hydrocarbon having from 3 to 12 carbon atoms and preferably from 6 to 12 carbon atoms. Illustrative of these hydrocarbons are propane, butane, pentane, hexane, octane, decane, dodecane, 2,2-dimethylbutane, 2,2,3-trimethylbutane, 3,3-dimethylhexane, and 2,2,5-trimethylhexane. A single hydrocarbon or a mixture of hydrocarbons may be used as the reaction medium. Among the useful mixtures of hydrocarbons are such petroleum fractions as VMP naphtha and mineral spirits.

The amount of the reaction medium used is that which will impart the desired fluidity to the reaction mixture and at the same time improve its heat transfer characteristics so that the heat evolved can be removed rapidly and the reaction can be carried out at a temperature at which very little by-product formation takes place.

During the course of the reaction, small amounts of the medium are usually removed from the reaction vessel along with the crude product. The medium lost in this way may be recovered when the crude product is heated under subatmospheric pressure to remove low-boiling impurities from it. The recovered reaction medium may be returned to the reaction vessel along with the amount of fresh medium which is required to replace that lost during the removal of the product. Alternatively, the recovered medium may be discarded and fresh medium used to bring the amount of medium in the reaction vessel to the desired level.

While the process of this invention is usually and preferably carried out continuously, it can also be carried out as a discontinuous or batch process. In the discontinuous mode of operation, approximately equimolar amounts of allyl alcohol and bromine are added to a reaction medium that is immiscible with 2,3-dibromo-1-propanol. The reaction mixture separates into two phases and the lower, product-containing phase is separated and then heated to remove low-boiling impurities from it. The upper phase may, if desired, be used as the reaction medium in the preparation of an additional quantity of 2,3-dibromo-1-propanol.

The invention is further illustrated by the following examples.

EXAMPLE 1

The preparation of 2,3-dibromo-1-propanol was carried out in a jacketed reaction vessel equipped with a thermometer, an agitator, and three dropping funnels. The vessel had a bottom outlet joined to it through a small (ca 5 cc.) chamber. During the bromination reaction, ice water was circulated through the jacket of the reaction vessel, and the reaction mixture was agitated vigorously.

One hundred grams of n-hexane was charged to the reaction vessel. Then, over a period of 2.5 hours, 1600 grams (10.01 moles; 520 cc.) of bromine and 600 grams (10.33 mole; 700 cc.) of allyl alcohol were added simultaneously and continuously at the rate of 1.345 parts by volume of allyl alcohol per part by volume of bromine while the reaction mixture was agitated vigorously and maintained at 20°–30°C.

The reaction mixture became turbid shortly after the start of the addition of the reactants, and a small amount of a hexaneimmiscible lower phase soon appeared in the chamber leading to the bottom outlet of the reaction vessel. The lower phase, which comprised crude 2,3-dibromo-1-propanol, was withdrawn continuously at such a rate that the interface between the hexane phase and the hexane-immiscible phase remained in the chamber. When the addition of allyl alcohol and bromine was completed, 2240 grams of crude 2,3-dibromo-1-propanol had been removed from the reaction vessel, and 55 grams of the hexane layer remained in it.

The crude dibromopropanol was distilled under subatmospheric pressure in the presence of a small amount of dry soda ash. After the hexane and other low boiling materials had been removed, there was obtained 1865 grams (85.6% yield) of 2,3-dibromo-1-propanol as the main fraction. The product was shown by gas chromatography to contain 99.7% of 2,3-dibromo-1-propanol and 0.2% of 1,2,3-tribromopropane.

EXAMPLE 2

To 150 grams (225 cc.) of n-hexane in the reaction vessel described in Example 1 were added simultaneously and continuously 4000 grams (25.03 moles) of bromine and 1515 grams (26.08 moles) of allyl alcohol at the rate of 1.35 parts by volume of allyl alcohol per part by volume of bromine. During the addition of bromine and allyl alcohol, which required 6 hours, the reaction mixture was maintained at 20°–30°C. The lower, hexane-immiscible phase that formed was withdrawn continuously from the bottom outlet, as described in Example 1. When about 80% of the bromine and allyl alcohol had been added, an additional 33.5 grams (50 cc.) of n-hexane was added to the reaction mixture.

When the addition of the reactants was complete, 5630 grams of crude 2,3-dibromo-1-propanol had been removed from the reaction vessel, and 77 grams of the hexane layer remained in it.

A 1450 gram (6.44 moles) aliquot of the crude 2,3-dibromo-1-propanol was distilled under subatmospheric pressure in the presence of a small amount of dry soda ash. After hexane and other low-boiling materials had been removed, there was obtained 1194 grams (5.48 moles; 85.1% yield) of 2,3-dibromo-1-propanol as the main fraction. The product was shown by gas chromatography to contain 99.7% of 2,3-dibromo-1-propanol and 0.1% of 1,2,3-tribromopropane.

EXAMPLE 3

Using the procedure described in Example 1, 1600 grams (10.01 moles) of bromine and 600 grams (10.33 moles) of allyl alcohol were added simultaneously and continuously to 100 grams of n-heptane. The reaction mixture was maintained at 20°–30°C. during the 2.75 hour addition period. The lower, heptane-immiscible layer that formed was removed continuously from the reaction vessel, as is described in Example 1.

When the addition of the reactants was complete, 2223 grams of crude 2,3-dibromo-1-propanol had been removed from the reaction vessel, and 61.6 grams of the heptane layer remained in it.

A 1366 gram aliquot, which represented 6.15 moles of bromine, was distilled under subatmospheric pressure in the presence of a small amount of dry soda ash. After heptane and other low-boiling materials had been removed, 1157 grams (5.31 moles) of 2,3-dibromo-1-propanol was obtained as the main fraction.

The product, which was obtained in an 86.3% yield, was shown by gas chromatography to contain 99.9% of 2,3-dibromo-1-propanol and less than 0.05% of 1,2,3-tribromopropane.

EXAMPLE 4

Using the procedure described in Example 1, 1600 grams (10.01 moles) of bromine and 600 grams (10.33 moles) of allyl alcohol were added simultaneously and continuously to 100 grams of mineral spirits, which had a boiling range of 165°–192.5°C. and which contained less than 8% of aromatic compounds. The addition took place over a period of 2.25 hours during which the reaction mixture was agitated and maintained at 25°–35°C. The lower, mineral spirits-immiscible layer that formed was removed continuously from the reaction vessel, as described in Example 1.

When the addition of the reactants was complete, 2232 grams of crude 2,3-dibromo-1-propanol had been removed from the reaction vessel, and 70.5 grams of mineral spirits remained in it.

A 1326 gram aliquot, which represented 5.95 moles of bromine, was distilled under subatmospheric pressure in the presence of a small amount of dry soda ash. There was obtained 1117 grams (5.126 moles; 86.2% yield) of 2,3-dibromo-1-propanol as the main fraction. The product was shown by gas chromatography to contain 99.9% of 2,3-dibromo-1-propanol and less than 0.05% of 1,2,3-tribromopropane.

What is claimed is:

1. The process for the production of 2,3-dibromo-1-propanol that comprises contacting allyl alcohol with an approximately equimolar amount of bromine at a temperature between −10°C. and 60°C. and in the presence of a reaction medium that comprises a saturated aliphatic hydrocarbon having 3 to 12 carbon atoms and thereafter separating 2,3-dibromo-1-propanol from said reaction medium.

2. The process of claim 1 wherein the reaction medium is a saturated aliphatic hydrocarbon having 6 to 12 carbon atoms.

3. In the process for the continuous production of 2,3-dibromo-1-propanol wherein allyl alcohol and bromine in approximately equimolar quantities are added simultaneously and continuously to a reaction vessel containing a reaction medium while the temperature of the reaction medium is maintained between −10°C. and 60°C. and 2,3-dibromo-1-propanol is removed continuously from the reaction vessel, the improvement that comprises adding allyl alcohol and bromine to a reaction medium that is a saturated aliphatic hydrocarbon having 3 to 12 carbon atoms.

4. The process of claim 3 wherein the reaction medium comprises a saturated aliphatic hydrocarbon having 6 to 12 carbon atoms.

5. The process of claim 3 wherein the reaction medium is hexane.

6. The process of claim 3 wherein the reaction medium is heptane.

7. The process of claim 3 wherein the reaction medium is mineral spirits.

8. The process of claim 3 wherein the temperature of the reaction medium is maintained between 10°C. and 40°C.

* * * * *